(12) United States Patent  (10) Patent No.: US 7,796,045 B2
Spear et al.  (45) Date of Patent: Sep. 14, 2010

(54) SYSTEM AND METHOD FOR MANAGING WORKFLOW

(75) Inventors: Steven E. Spear, Centerville, MN (US); Wendy R. Larson, Little Canada, MN (US); Jeffrey A. Martin, Circle Pines, MN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 12/258,654

(22) Filed: Oct. 27, 2008

(65) Prior Publication Data

US 2009/0051526 A1  Feb. 26, 2009

Related U.S. Application Data

(63) Continuation of application No. 11/325,776, filed on Jan. 5, 2006, now Pat. No. 7,443,303.

(60) Provisional application No. 60/642,775, filed on Jan. 10, 2005.

(51) Int. Cl.
G08B 23/00 (2006.01)
(52) U.S. Cl. .............. 340/573.1; 340/573.4; 340/572.1; 340/572.4; 340/572.8; 340/539.11; 340/539.12; 340/686.1; 340/686.6; 600/300; 600/515; 600/518; 705/8; 705/9
(58) Field of Classification Search .............. 340/573.1, 340/573.4, 572.1, 572.4, 572.8, 539.11, 539.12, 340/686.1, 686.6; 600/300, 515, 518; 705/8, 705/9
See application file for complete search history.

(56) References Cited

U.S. PATENT DOCUMENTS 3,656,687 A  4/1972  Romney et al.
3,970,996 A  7/1976  Yasaka et al.

(Continued)

FOREIGN PATENT DOCUMENTS

FR  2 844 375  3/2004

(Continued)

OTHER PUBLICATIONS

Vince Stanford, "Beam Me Up, Doctor McCoy", IEEE Pervasive Computing, vol. 02, No. 3, Sep. 2003(, pp. 13-18.

(Continued)

Primary Examiner—Tai T Nguyen
(74) Attorney, Agent, or Firm—Barnes & Thornburg LLP

(57) ABSTRACT

A system and method for managing workflow is provided. The system includes one or more computer devices which execute workflow software to assign tasks to medical staff. The workflow software may be configured to assign tasks to persons on the medical staff based on a set of criteria including the person's current location or zone, the locations or zones in which other uncompleted tasks are located, and whether the person has a particular pieced of medical equipment. The system may include portable wireless communication devices and an interactive voice recognitions (IVR) subsystem to permit persons on the staff to communicate information by voice to the computer devices via the portable wireless communication devices and to receive audio messages from the computer devices via the wireless communication devices. The workflow software may be configured to display a staff screen in which the displayed data is filtered by medical staff role and sorted by medical staff identification.

20 Claims, 5 Drawing Sheets

U.S. PATENT DOCUMENTS

| | | |
|---|---|---|
| 4,116,470 A | 9/1978 | Johnsen |
| 4,121,574 A | 10/1978 | Lester |
| 4,130,881 A | 12/1978 | Haessler et al. |
| 4,159,129 A | 6/1979 | Lockhart |
| 4,221,404 A | 9/1980 | Shuffstall |
| 4,228,506 A | 10/1980 | Ripley et al. |
| 4,275,385 A | 6/1981 | White |
| 4,277,089 A | 7/1981 | Lockhart |
| 4,290,114 A | 9/1981 | Sinay |
| 4,370,983 A | 2/1983 | Lichtenstein |
| 4,464,172 A | 8/1984 | Lichtenstein |
| 4,489,387 A | 12/1984 | Lamb et al. |
| 4,533,221 A | 8/1985 | Trachtman |
| 4,572,891 A | 2/1986 | Drexler |
| 4,622,013 A | 11/1986 | Cerchio |
| 4,625,276 A | 11/1986 | Benton et al. |
| 4,665,004 A | 5/1987 | Drexler |
| 4,667,292 A | 5/1987 | Mohlenbrock et al. |
| 4,792,968 A | 12/1988 | Katz |
| 4,799,712 A | 1/1989 | Biava et al. |
| 4,803,625 A | 2/1989 | Fu et al. |
| 4,835,372 A | 5/1989 | Gombrich et al. |
| 4,845,739 A | 7/1989 | Katz |
| 4,850,009 A | 7/1989 | Zook et al. |
| 4,855,842 A | 8/1989 | Hayes et al. |
| 4,857,713 A | 8/1989 | Brown |
| 4,857,716 A | 8/1989 | Gombrich et al. |
| 4,858,121 A | 8/1989 | Barber et al. |
| 4,869,531 A | 9/1989 | Rees |
| 4,878,175 A | 10/1989 | Norden-Paul et al. |
| 4,893,270 A | 1/1990 | Beck et al. |
| 4,916,441 A | 4/1990 | Gombrich |
| 4,918,572 A | 4/1990 | Tarver et al. |
| 4,937,743 A | 6/1990 | Rassman et al. |
| 4,939,508 A | 7/1990 | Lawrence et al. |
| 4,945,476 A | 7/1990 | Bodick et al. |
| 4,945,477 A | 7/1990 | Edwards |
| 4,947,152 A | 8/1990 | Hodges |
| 4,962,473 A | 10/1990 | Crain |
| 4,974,607 A | 12/1990 | Miwa |
| 4,975,842 A | 12/1990 | Darrow et al. |
| 4,987,538 A | 1/1991 | Johnson et al. |
| 4,990,892 A | 2/1991 | Guest et al. |
| 5,001,630 A | 3/1991 | Wiltfong |
| 5,006,699 A | 4/1991 | Felkner et al. |
| 5,016,172 A | 5/1991 | Dessertine |
| 5,018,067 A | 5/1991 | Mohlenbrock et al. |
| 5,019,976 A | 5/1991 | Chiu et al. |
| 5,025,374 A | 6/1991 | Roizen et al. |
| 5,033,009 A | 7/1991 | Dubnoff |
| 5,048,075 A | 9/1991 | Katz |
| 5,054,096 A | 10/1991 | Beizer |
| 5,065,315 A | 11/1991 | Garcia |
| 5,070,383 A | 12/1991 | Sinar et al. |
| 5,070,452 A | 12/1991 | Doyle, Jr. et al. |
| 5,072,383 A | 12/1991 | Brimm et al. |
| 5,077,666 A | 12/1991 | Brimm et al. |
| 5,099,424 A | 3/1992 | Schneiderman |
| 5,101,476 A | 3/1992 | Kukla |
| 5,121,470 A | 6/1992 | Trautman |
| 5,133,045 A | 7/1992 | Gaither et al. |
| 5,136,502 A | 8/1992 | Van Remortel et al. |
| 5,140,519 A | 8/1992 | Friesdorf et al. |
| 5,146,562 A | 9/1992 | Kukla |
| 5,148,366 A | 9/1992 | Buchanan et al. |
| 5,193,855 A | 3/1993 | Shamos |
| 5,208,907 A | 5/1993 | Shelton et al. |
| 5,225,976 A | 7/1993 | Tawil |
| 5,235,510 A | 8/1993 | Yamada et al. |
| 5,235,702 A | 8/1993 | Miller |
| 5,247,611 A | 9/1993 | Norden-Paul et al. |
| 5,253,164 A | 10/1993 | Holloway et al. |
| 5,253,361 A | 10/1993 | Thurman et al. |
| 5,253,362 A | 10/1993 | Nolan et al. |
| 5,255,309 A | 10/1993 | Katz |
| 5,259,023 A | 11/1993 | Katz |
| 5,262,943 A | 11/1993 | Thibado et al. |
| 5,265,010 A | 11/1993 | Evans-Paganelli et al. |
| 5,269,155 A | 12/1993 | Adelmann |
| 5,272,625 A | 12/1993 | Nishihara et al. |
| 5,274,749 A | 12/1993 | Evans |
| 5,276,805 A | 1/1994 | Hamaguchi |
| 5,277,188 A | 1/1994 | Selker |
| 5,287,459 A | 2/1994 | Gniewek |
| 5,291,399 A | 3/1994 | Chaco |
| 5,292,029 A | 3/1994 | Pearson |
| 5,296,688 A | 3/1994 | Hamilton et al. |
| 5,297,216 A | 3/1994 | Sklarew |
| 5,301,319 A | 4/1994 | Thurman et al. |
| 5,305,748 A | 4/1994 | Wilk |
| 5,307,262 A | 4/1994 | Ertel |
| 5,307,263 A | 4/1994 | Brown |
| 5,319,363 A | 6/1994 | Welch et al. |
| 5,319,543 A | 6/1994 | Wilhelm |
| 5,324,077 A | 6/1994 | Kessler et al. |
| 5,325,293 A | 6/1994 | Dorne |
| 5,325,478 A | 6/1994 | Shelton et al. |
| 5,327,341 A | 7/1994 | Whalen et al. |
| 5,331,549 A | 7/1994 | Crawford, Jr. |
| 5,343,869 A | 9/1994 | Pross et al. |
| 5,361,202 A | 11/1994 | Doue |
| 5,426,425 A | 6/1995 | Conrad et al. |
| 5,441,047 A | 8/1995 | David et al. |
| 5,458,123 A | 10/1995 | Unger |
| 5,471,382 A | 11/1995 | Tallman et al. |
| 5,473,537 A | 12/1995 | Glazer et al. |
| 5,515,492 A | 5/1996 | Li et al. |
| 5,517,405 A | 5/1996 | McAndrew et al. |
| 5,544,044 A | 8/1996 | Leatherman |
| 5,546,580 A | 8/1996 | Seliger et al. |
| 5,557,514 A | 9/1996 | Seare et al. |
| 5,561,412 A | 10/1996 | Novak et al. |
| 5,576,952 A | 11/1996 | Stutman et al. |
| 5,583,758 A | 12/1996 | McIlroy et al. |
| 5,592,945 A | 1/1997 | Fiedler |
| 5,594,637 A | 1/1997 | Eisenberg et al. |
| 5,594,638 A | 1/1997 | Iliff |
| 5,596,750 A | 1/1997 | Li et al. |
| 5,606,679 A | 2/1997 | Cohn et al. |
| 5,664,207 A | 9/1997 | Crumpler et al. |
| 5,700,704 A | 12/1997 | Ikeda et al. |
| 5,713,350 A | 2/1998 | Yokota et al. |
| 5,748,907 A | 5/1998 | Crane |
| 5,752,976 A | 5/1998 | Duffin et al. |
| 5,760,704 A | 6/1998 | Barton et al. |
| 5,765,139 A | 6/1998 | Bondy |
| 5,767,751 A | 6/1998 | Magnusson |
| 5,822,544 A | 10/1998 | Chaco et al. |
| 5,823,948 A | 10/1998 | Ross, Jr. et al. |
| 5,826,237 A | 10/1998 | Macrae et al. |
| 5,838,223 A | 11/1998 | Gallant et al. |
| 5,842,175 A | 11/1998 | Andros et al. |
| 5,845,253 A | 12/1998 | Rensimer et al. |
| 5,867,821 A | 2/1999 | Ballantyne et al. |
| 5,899,998 A | 5/1999 | McGauley et al. |
| 5,907,490 A | 5/1999 | Oliver |
| 5,913,197 A | 6/1999 | Kameda |
| 5,923,018 A | 7/1999 | Kameda et al. |
| 5,946,659 A | 8/1999 | Lancelot et al. |
| 5,970,466 A | 10/1999 | Detjen et al. |
| 5,974,389 A | 10/1999 | Clark et al. |
| 6,003,011 A | 12/1999 | Sarin et al. |
| 6,023,702 A | 2/2000 | Leisten et al. |
| 6,047,259 A | 4/2000 | Campbell et al. |

| Patent/Pub No. | Date | Name |
|---|---|---|
| 6,067,548 A | 5/2000 | Cheng |
| 6,083,248 A | 7/2000 | Thompson |
| 6,277,071 B1 | 8/2001 | Hennessy et al. |
| 6,321,203 B1 | 11/2001 | Kameda |
| 6,334,133 B1 | 12/2001 | Thompson et al. |
| 6,347,329 B1 | 2/2002 | Evans |
| 6,385,589 B1 | 5/2002 | Trusheim et al. |
| 6,401,072 B1 | 6/2002 | Haudenschild et al. |
| 6,401,138 B1 | 6/2002 | Judge et al. |
| 6,421,649 B1 | 7/2002 | Rattner |
| 6,434,531 B1 | 8/2002 | Lancelot et al. |
| 6,445,300 B1 | 9/2002 | Luman |
| 6,601,234 B1 | 7/2003 | Bowman-Amuah |
| 6,640,134 B2 | 10/2003 | Raymond et al. |
| 6,714,913 B2 | 3/2004 | Brandt et al. |
| 6,785,721 B1 | 8/2004 | Immerman et al. |
| 6,825,763 B2 | 11/2004 | Ulrich et al. |
| 6,850,895 B2 | 2/2005 | Brodersen et al. |
| 6,870,913 B2 | 3/2005 | Narasimhan et al. |
| 6,876,303 B2 | 4/2005 | Reeder et al. |
| 6,901,255 B2 | 5/2005 | Shostak |
| 6,915,254 B1 | 7/2005 | Heinze et al. |
| 6,998,978 B2 | 2/2006 | Kirkeby |
| 7,443,303 B2 * | 10/2008 | Spear et al. ............... 340/573.1 |
| 2001/0044738 A1 | 11/2001 | Elkin et al. |
| 2002/0007300 A1 | 1/2002 | Slatter |
| 2002/0016722 A1 | 2/2002 | Kameda |
| 2002/0029161 A1 | 3/2002 | Brodersen et al. |
| 2002/0055855 A1 | 5/2002 | Cule et al. |
| 2002/0062367 A1 | 5/2002 | Debber et al. |
| 2002/0073114 A1 | 6/2002 | Nicastro et al. |
| 2002/0078432 A1 | 6/2002 | Charisius et al. |
| 2002/0107914 A1 | 8/2002 | Charisius et al. |
| 2002/0111831 A1 | 8/2002 | Harada |
| 2002/0165733 A1 | 11/2002 | Pulkkinen et al. |
| 2002/0165898 A1 | 11/2002 | Duffy et al. |
| 2002/0173991 A1 | 11/2002 | Avitall |
| 2002/0183979 A1 | 12/2002 | Wildman |
| 2002/0188597 A1 | 12/2002 | Kern et al. |
| 2003/0013146 A1 | 1/2003 | Werb |
| 2003/0018510 A1 | 1/2003 | Sanches |
| 2003/0045958 A1 | 3/2003 | Brandt et al. |
| 2003/0052787 A1 | 3/2003 | Zerhusen et al. |
| 2003/0065546 A1 | 4/2003 | Gorur et al. |
| 2003/0069025 A1 | 4/2003 | Hoctor et al. |
| 2003/0073434 A1 | 4/2003 | Shostak |
| 2003/0074222 A1 | 4/2003 | Rosow et al. |
| 2003/0090387 A1 | 5/2003 | Lestienne et al. |
| 2003/0149714 A1 | 8/2003 | Casati et al. |
| 2003/0154232 A1 | 8/2003 | Beringer et al. |
| 2003/0174049 A1 | 9/2003 | Beigel et al. |
| 2003/0177030 A1 | 9/2003 | Turner et al. |
| 2003/0177370 A1 | 9/2003 | Smith |
| 2003/0195644 A1 | 10/2003 | Borders et al. |
| 2003/0204431 A1 * | 10/2003 | Ingman ........................ 705/9 |
| 2004/0019501 A1 | 1/2004 | White et al. |
| 2004/0073453 A1 | 4/2004 | Nenov et al. |
| 2004/0078231 A1 | 4/2004 | Wilkes et al. |
| 2004/0078373 A1 | 4/2004 | Ghoneimy et al. |
| 2004/0193449 A1 | 9/2004 | Wildman et al. |
| 2004/0243444 A1 | 12/2004 | Steusloff et al. |
| 2004/0249674 A1 | 12/2004 | Eisenberg et al. |
| 2004/0267589 A1 | 12/2004 | Wallman |
| 2005/0004825 A1 | 1/2005 | Ehrler et al. |
| 2005/0015742 A1 | 1/2005 | Wood et al. |
| 2005/0021348 A1 | 1/2005 | Chan et al. |
| 2005/0021369 A1 | 1/2005 | Cohen et al. |
| 2005/0021383 A1 | 1/2005 | Fliess et al. |
| 2005/0027696 A1 | 2/2005 | Swaminathan et al. |
| 2005/0033598 A1 | 2/2005 | Knapp et al. |
| 2005/0035862 A1 | 2/2005 | Wildman et al. |
| 2005/0055242 A1 | 3/2005 | Bello et al. |
| 2005/0055244 A1 | 3/2005 | Mullan et al. |
| 2005/0071190 A1 | 3/2005 | Herger et al. |
| 2005/0075902 A1 | 4/2005 | Wager et al. |
| 2005/0075904 A1 | 4/2005 | Wager et al. |
| 2005/0086303 A1 | 4/2005 | Ye et al. |
| 2005/0091098 A1 | 4/2005 | Brodersen et al. |
| 2005/0091304 A1 | 4/2005 | Trayler |
| 2005/0108396 A1 | 5/2005 | Bittner |
| 2005/0125256 A1 | 6/2005 | Schoenberg et al. |
| 2005/0131740 A1 | 6/2005 | Massenzio et al. |
| 2006/0143045 A1 | 6/2006 | Nacey |
| 2006/0167738 A1 | 7/2006 | Spear et al. |
| 2007/0067199 A1 | 3/2007 | Shine et al. |
| 2008/0065430 A1 | 3/2008 | Rosow et al. |
| 2008/0065431 A1 | 3/2008 | Rosow et al. |
| 2008/0065432 A1 | 3/2008 | Rosow et al. |
| 2008/0065433 A1 | 3/2008 | Rosow et al. |
| 2008/0065434 A1 | 3/2008 | Rosow et al. |
| 2008/0221926 A1 | 9/2008 | Rosow et al. |
| 2008/0312971 A2 | 12/2008 | Rosow et al. |
| 2008/0312972 A2 | 12/2008 | Rosow et al. |
| 2008/0312973 A2 | 12/2008 | Rosow et al. |
| 2008/0312974 A2 | 12/2008 | Rosow et al. |
| 2008/0312975 A2 | 12/2008 | Rosow et al. |

FOREIGN PATENT DOCUMENTS

| | | |
|---|---|---|
| WO | WO 97/15021 | 4/1997 |
| WO | WO 98/59487 | 12/1998 |
| WO | WO 99/04043 | 1/1999 |
| WO | WO 00/41104 | 7/2000 |
| WO | WO 2004/021149 | 3/2004 |
| WO | WO 2004/036390 A2 | 4/2004 |
| WO | WO 2004/036390 A3 | 4/2004 |

OTHER PUBLICATIONS

Garwood G. J. et al. "Work Management System", British Telecommunications Engineering, London, GB, vol. 10, No. 3, Oct. 1, 1991, pp. 204-210.

Kristen Kenedy, "Location-Based Technology for Wi-Fi Networks Highlighted at DemoMobile", www.crn.com (online), Sep. 20, 2002.

Hochmuth, Phil, "VoIP unwired", www.networkworld.com, (online), Jul. 28, 2003, pp. 1-3.

NaviCare® System User Manual, draft dated Nov. 29, 2004, (141 pages).

NaviCare® System Implementation Binder, draft dated Nov. 29, 2004, (54 pages).

U.S. Appl. No. 08/407,218, filed Mar. 20, 1995, now abandoned, titled: "Critical Path Flow Tool and Method Application", (73 pages), Appendix 4 of the U.S. Appl. No. 60/642,775.

* cited by examiner

Fig. 2

SYSTEM AND METHOD FOR MANAGING WORKFLOW

This application is a continuation of U.S. application Ser. No. 11/325,776, filed Jan. 5, 2006, which issued as U.S. Pat. No. 7,443,303 on Oct. 28, 2008, and which claimed the benefit under 35 U.S.C. §119(e), of U.S. Provisional Patent Application No. 60/642,775 which was filed Jan. 10, 2005, each of which is hereby incorporated by reference herein in its entirety.

BACKGROUND OF THE INVENTION

The present disclosure relates to systems and methods for managing workflow, and particularly, to systems and methods for managing the workflow of medical staff in a healthcare facility. More particularly, the present disclosure relates to systems and methods for assigning tasks to medical staff.

Computer-based systems used in healthcare facilities, such as hospitals, to manage workflow and assign tasks to the medical staff, such as nurses, orderlies, transporters, housekeeping personal, and the like, are known. The NaviCare® system, version 5.2, (referred to hereafter as "NaviCare® 5.2 system") marketed by Hill-Rom Company, Inc. is one such example. Details of the NaviCare® 5.2 system are shown and described in the Appendices forming part of U.S. Provisional Patent Application Ser. No. 60/642,775 to which the present application claims priority and which is incorporated by reference herein. In some known workflow systems, as tasks are completed or events transpire, this data is entered substantially in real time by medical staff via key presses, mouse clicks, or touch of a screen at monitoring stations located throughout the healthcare facility.

The NaviCare® 5.2 system includes software that is executed to provide a tabular display of the status of patients, tasks that need to be performed, patient information, status of rooms, patient location, and other information at the various monitoring stations or displays located throughout the hospital. The NaviCare® 5.2 system allows medical staff to track the status of patients as the patients move throughout the hospital. In the NaviCare® 5.2 system, many of the various tasks that need to be performed, information about patients, and other information are represented by icons on the displayed tables. Exemplary icons include a bucket icon to indicate that room cleanup is needed, a gurney icon to indicate that the patient is ready for transport or is being transported, a house icon to indicate that the patient has been discharged, and a scalpel icon to indicate that a medical procedure is underway, just to name a few.

SUMMARY OF THE INVENTION

A system and/or a method for managing workflow is provided and comprises one or more of the features recited in the appended claims and/or the following features which, alone or in any combination, may comprise patentable subject matter:

The system may receive information indicating that a person on a medical staff of a healthcare facility has completed an assigned task. The system may determine the person's location in the healthcare facility. The system may execute a shortest-path algorithm to determine at least one path length between the person's location and at least one other location associated with at least one other task. The system may assign a new task to the person based on a set of criteria including the at least one path length. The path lengths may either be indicative of an estimated amount of time for the person to travel from the person's current location to another location or be indicative of an estimated distance between the person's current location and another location. The shortest-path algorithm may comprise Dijkstra's algorithm or any other suitable algorithm, such as an array sorting algorithm to sort path length data stored in an array. Prior to executing the shortest-path algorithm, locations in which no tasks need to be performed may be eliminated from consideration to reduce computational time of the system.

According to the shortest-path algorithm, a vertex may be assigned to each of a plurality of locations throughout the healthcare facility and at least one edge condition may be designated between each vertex and at least one other vertex. Each edge condition may correspond either to an estimated time of travel between the associated vertices or to a distance between the associated vertices or both. The edge conditions may comprise bidirectional edge conditions such that the edge condition in one direction between two vertices is not equal to the edge condition in an opposite direction between the same two vertices. The locations to which vertices are assigned may correspond to, for example, a room of the healthcare facility, a zone of the healthcare facility, a care unit of the healthcare facility, or a transition point in the healthcare facility. The transition points may be associated with, for example, an elevator, an escalator, a flight of stairs, a ramp, a corridor, and the like.

The system may receive information indicating that the person on the medical staff has completed an assigned task via an interactive voice response (IVR) portion of the system. The IVR portion of the system may receive voice information either via a wireless communication device carried by the person, via a telephone of the healthcare facility, or via other types of computer devices having voice communication capability. The system may determine the person's location in the healthcare facility based on a wireless signal received from a portable device carried by the person or by associating the person's location with a monitoring station at which the person enters the information indicating that the person has completed the assigned task. The portable device may comprise a badge or tag worn by the person. In order to track the location of equipment in the healthcare facility, the system may also receive wireless signals transmitted by transmitters coupled to pieces of equipment. Badges or tags similar to those worn by the medical staff may also be used to track equipment.

Other criteria that the system may factor into the determination of what tasks to assign to a particular person of the medical staff may include whether the person is in possession of a particular type of medical equipment and/or the role that has been assigned to the person. For example, if the role assigned to the person is the role of being a transporter, the set of criteria may include an amount of time that a patient or a piece of equipment has been waiting to be transported from one location to another.

A system for managing workflow, including assigning tasks to medical staff in a healthcare facility having a computer network, is provided. The system may comprise a computer device that is coupled to the computer network and that executes workflow software. The workflow software may be configured to associate tasks that need to be performed with patients and with locations in the healthcare facility and to assign to the medical staff selected ones of the tasks that need to be performed. The system may further comprise a portable wireless communication device carried by at least one person of the medical staff. The system may have a wireless transceiver coupled to computer network. The wireless transceiver may be configured for two way wireless communication with the portable wireless communication device.

The system may comprise an interactive voice recognition (IVR) subsystem that is coupled via the computer network to the at least one computer device and to the wireless transceiver. Voice communications spoken by the person to indicate that an assigned task has been completed may be communicated to the IVR subsystem via the portable wireless communication device, the wireless transceiver, and the computer network. The voice communications may be transformed by the IVR subsystem into data that is sent to the at least one computer device. The at least one computer device may operate in accordance with the workflow software to assign another task to the caregiver in response to the data received from the IVR subsystem indicating that the person has completed the assigned task.

In accordance with the teachings of this disclosure, a system for managing workflow, including assigning tasks to medical staff in a healthcare facility having a computer network, may comprise a memory device to store data regarding patient identification, patient status, patient location, tasks that need to be performed by medical staff, medical staff identification, and medical staff roles. The system may further comprise a processor operably coupled to the memory device and operable to execute workflow software to associate the tasks that need to be performed with patients and with locations in the healthcare facility and to assign to the medical staff selected ones of the tasks that need to be performed. The system may also have a display operably coupled to the processor. The display may be signaled by the processor to display at least one of a plurality of screens with at least some of the screens displaying at least some of the data stored in the memory device. At least one of the plurality of screens may be a staff screen in which the displayed data is filtered by medical staff role and sorted by medical staff identification.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the following figures, in which:

FIG. 2 is a screen shot of a bed board screen showing the status of patient beds in rooms associated with various zones of the healthcare facility;

DETAILED DESCRIPTION OF THE DRAWINGS

Figure 1:
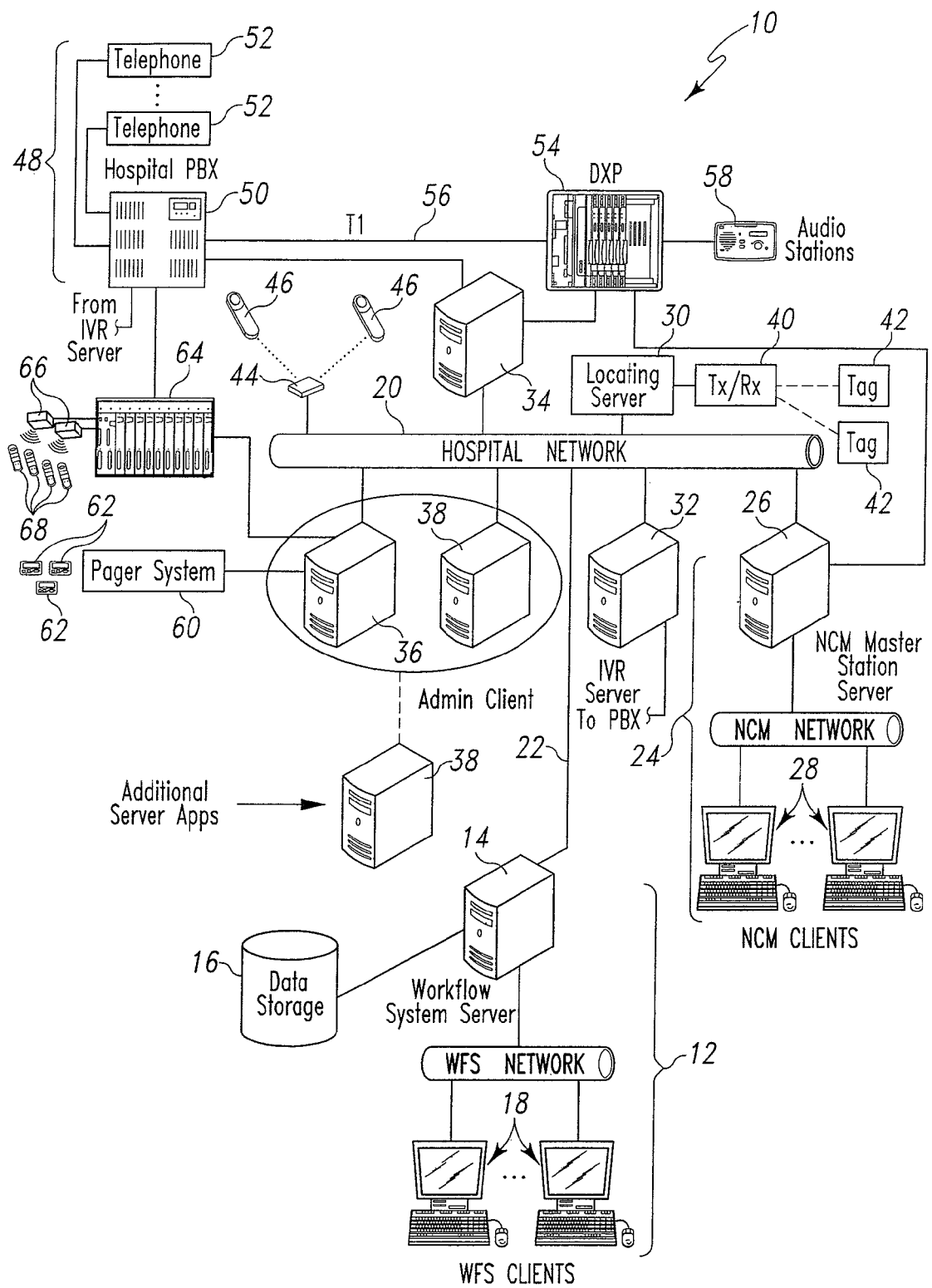
FIG. 1 is a block diagram showing various components of a network of devices in a healthcare facility, the network including a workflow system (WFS) including a WFS server which executes workflow software, a number of WFS client personal computers (PC's), and a data storage device.

A network 10 of a healthcare facility includes a workflow system 12 that includes a workflow system (WFS) server 14, a data storage device 16, and one or more WFS client personal computers (PC's) 18 as shown diagrammatically in FIG. 1. Server 14 is coupled to hospital network infrastructure 20 via a wired or wireless communication link 22. The architecture of network 10 is generally at the discretion of information technology personnel of the healthcare facility and may include additional pieces of hardware (not shown) such as routers, backup power systems, and medical equipment, such as patient monitors, hospital beds, X-ray systems, and so on having networking capability. Devices such as servers, PC's, data storage devices, and any other pieces of hardware or equipment having processors, such as microprocessors, microcontrollers, field programmable gate arrays, programmable logic controllers, or other logic-based components for processing data, are considered to be computer devices according to this disclosure.

In the illustrative example, a nurse call system 24 is also included in network 10 and includes a nurse call system server 26 and associated PC's 28. Network 10 further includes a locating server 30, an interactive voice recognition (IVR) server 32, a first communication system server 34, a second communication system server 36, and a plurality of additional servers 38. Illustratively, only two servers 38 are shown, but are intended to be representative of all of the other servers that are included in network 10. Each of the various servers 14, 26, 30, 32, 34, 36, 38 has a processor (not shown) for executing associated application software. Of primary interest in the present disclosure is the workflow software of server 14 and PC's 18.

It is contemplated by this disclosure that each of servers 14, 26, 30, 32, 34, 36, 38 may transmit data to, and receive data from, each of the other servers 14, 26, 30, 32, 34, 36, 38 so that the application software on each of servers 14, 26, 30, 32, 34, 36, 38 as access to data on each of the other servers 14, 26, 30, 32, 34, 36, 38. For example, locating server 30 is coupled to a plurality of transmitter and/or receiver units 40 which transmit and/or receive wireless signals to/from locating and tracking tags 42 that are mounted to pieces of equipment or carried by medical staff. One way that medical staff often carry tags 42 is by clipping or otherwise attaching the tags 42 to their clothing or by wearing the tags 42 on chains or cords around their necks. Tags 42 are sometimes referred to as "badges" by those in the art.

Locating server 30 executes software to track the whereabouts of equipment and persons on the medical staff throughout the associated healthcare facility based on wireless signals received by units 40 from tags 42. In some embodiments, units 40 periodically transmit a wireless query within a limited area of the healthcare facility and any tags 42 within the limited area respond by transmitting unique identification (ID) data which is received by an associated unit 40 and forwarded to server 30. Server 30 associates the unique ID data from the tags 42 with ID data, such as a serial number, of the corresponding unit 40 which receives the wireless transmission from the tags 42. During execution of the workflow software by server 14, if there is a need for data relating to the location of any equipment or persons being tracked by the locating-and-tracking software being executed by server 30, then server 14 sends a query to server 30 and server 30 responds with the requested information, if it is available. Alternatively, server 30 may periodically update server 14 with some or all of the data corresponding to the whereabouts of the equipment and persons being tracked and server 14 may store such data in the associated data storage device 16 for possible future use.

Communication server 34 executes application software to send and receive communication data to/from one or more communication units 44 which, in turn, communicate wirelessly with portable wireless communication devices 46 carried by persons on the medical staff. In the illustrative example, server 34, units 44, and devices 46 are configured to support voice communications between users of devices 46 and the other portions of the network 10. Server 34 determines what other portion of network 10 users of devices 46 are intending to communicate with and transmits data representative of the voice communications to that portion of network 10. For example, the healthcare systems standard telephone system includes one or more private branch exchanges (PBX's) 50 and a plurality of telephones 52. Server 34 is coupled to the one or more PBX's 50 to communicate therewith. Network 10 also includes one or more Digital Phone Switch (DXP) units 54 that are coupled to the PBX's via associated T1 lines 56. A plurality of Audio Stations 58 are located throughout the healthcare facility, typically in patient rooms, and are also coupled the DXP units 54. Thus, users of portable wireless communication devices 46 can speak to and hear from users of telephones 52 and users of audio stations 58.

In one embodiment, devices 46 and units 44 are the type marketed by Vocera Communications, Inc. of Cupertino, California and sold under the Vocera™ brand name. Such Vocera™ devices 46 (referred to sometimes as badges) may be worn by users in the same manner as tags 42 described above. The Vocera™ badges 46 and Vocera™ units 44 communicate over an 802.11b LAN infrastructure and also with the PBX's 50 via server 34 which executes associated Vocera™ server software. Devices 46 and units 44 which communicate according to wireless communications protocols other than 802.11b, such as the Bluetooth protocol, for example, are contemplated by this disclosure.

Illustrative network 10 also includes a pager system 60 which is coupled to server 36 and which includes a plurality of pagers 62 carried by some of the medical staff. Also coupled to server 36 and to PBX's 50 are one or more master control units 64 of a dedicated wireless telephone system of the health care facility. The dedicated wireless telephone system further includes a number of base stations 66 and number of wireless telephone handsets 68. As was the case with Vocera™ badges 46, handsets 68 are considered to be portable wireless communication devices according to this disclosure. While it is within the scope of this disclosure for network 10 to have any type of dedicated wireless telephone system, or none at all, in one embodiment, units 64, base stations 66, and handsets 68 are of the type marketed by Spectralink Corporation of Boulder, Colo. and/or ASCOM Ltd. of Berne, Switzerland. The Spectralink™ base stations 66 and handsets 68 communicate wirelessly via a scheme of frequency hopping spread spectrum over four TDMA channels in the 902-928 MHz radio frequency range. The Spectralink™ master control units 64 communicate with the PBX's 50 of system 10 either via a digital and/or an analog interface.

Server 14 and PC's 18 of workflow system 14 execute workflow software that has all of the functions and features of the NaviCare® 5.2 system software shown and described in the Appendices forming part of U.S. Provisional Patent Application Ser. No. 60/642,775 to which the present application claims priority and which is incorporated by reference herein. For the sake of brevity, these functions and features will not be described in this Detailed Description section. This disclosure contemplates workflow software that has additional functions and features not found in the NaviCare® 5.2 system software.

According to this disclosure, the workflow software of workflow system 12 is configured to respond to voice commands given by users carrying either portable wireless communication devices 46 or portable wireless communication devices 68. The IVR server 32 of network 10 executes application software to enable server 32 to receive voice communications from medical staff carrying devices 46, 68 via the PBX's 50 of network 10 and to convert those voice commands into signals that, in turn, are sent to server 14 for processing. Also, based on information communicated to IVR server 32 from server 14, IVR server 32 may generate one or more preprogrammed audio messages, or may create one or more new audio messages based on programming, that are communicated to users via devices 46, 68 and the associated servers and other equipment of network 10.

When a particular person on the medical staff initiates a call to workflow system 12 with one of devices 46, 68, server 14 notifies server 32 of the task which has been assigned to the associated person and server 32 responds by sending to the associated device 46, or device 68 as the case may be, audio messages that are specific to the assigned task. For example, if a person on the medical staff is assigned to transport a person or equipment from one place to another in the healthcare facility, when the person initiates a call to workflow system 12 with the respective device 46 or device 68, the IVR server 32 may respond with the following messages: "If you are done with the assigned transport, say 'done'... if you are delayed in performing the assigned transport, say 'delayed'... if you plan to take a break, say 'break.'" This is but one example and it will be appreciated that there are a vast number of tasks that the workflow software of system 12 is configured to assign to the medical staff and as such, there are a concomitant number of audio message menus with which the IVR system may be configured to communicate to the medical staff.

Depending upon the verbal statement or statements made by a person on the medical staff into the associated device 46, 68 in response to the audio message or messages generated by the IVR server 32, the workflow software of server 14 is executed, if appropriate, to update status information appearing on the screens of PC's 18. For example, if a person on the medical staff is assigned to transport a patient or piece of equipment and communicates verbally that the person is done with the task, then server 14 operates in accordance with the workflow software to remove the task from the list of tasks that need to be performed and date stamps the time of completion of the task for archiving purposes. Because the persons of the medical staff carrying devices 46, 68 are able to communicate via wireless voice communications with system 12, these persons no longer need to key in task status information on PC's 18, which are limited in number and located only at discrete locations throughout the healthcare facility. Thus, the medical staff carrying devices 46, 68 can communicate via wireless voice communications with system 12 while on the move, which saves time and increases productivity. This is believed to be an improvement over the prior art NaviCare® 5.2 system and also over a workflow system marketed by Tele-Tracking Technologies Inc. of Pittsburgh, Pa. which is believed to have interactive voice recognition capability, but only via the hard-wired, standard telephone system of the healthcare facility.

In accordance with this disclosure, the application software on servers 14, 26, 32, 34, 36, 38 may be placed on other ones of servers 14, 26, 32, 34, 36, 38 such that one or more of servers 14, 26, 32, 34, 36, 38 may be omitted from network 10. Thus, to give one example, the IVR application software on server 32 may instead reside on server 14 along with the workflow software. In some embodiments, the IVR application software and the workflow software may be combined into a single software package. In addition, data storage device 16 may be included as part of the memory of server 14 or as part of the memory of another server (not shown). In some embodiments, data storage device 16 may include other types of storage devices such as floppy or removable disk drives, a direct access storage device (DASD), a hard disk drive, a CD drive, a DVD drive, a tape drive, and the like that are included in, associated with, or coupled to server 14 and that read data stored on the corresponding type of data storage media (e.g. floppy disk, CD, DVD, tape, memory chip, etc.). Thus, system 12 may comprise multiple storage devices that are networked together and networked to server 14, as well as comprising a portion of the memory of server 14.

Furthermore, the various portions of network 10 which interact may be grouped together in any logical fashion and considered to be one system, with some portions of network 10 being considered subsystems of the designated system. Thus, servers 32, 34, 36, units 44, 64, and devices 44, 46 may be considered part of workflow system 12 with some of these servers, units, and devices being grouped into subsystems. In those embodiments in which IVR application software resides in server 14, then server 14 itself may be considered to form part of a workflow subsystem and an IVR subsystem.

Figure 2:
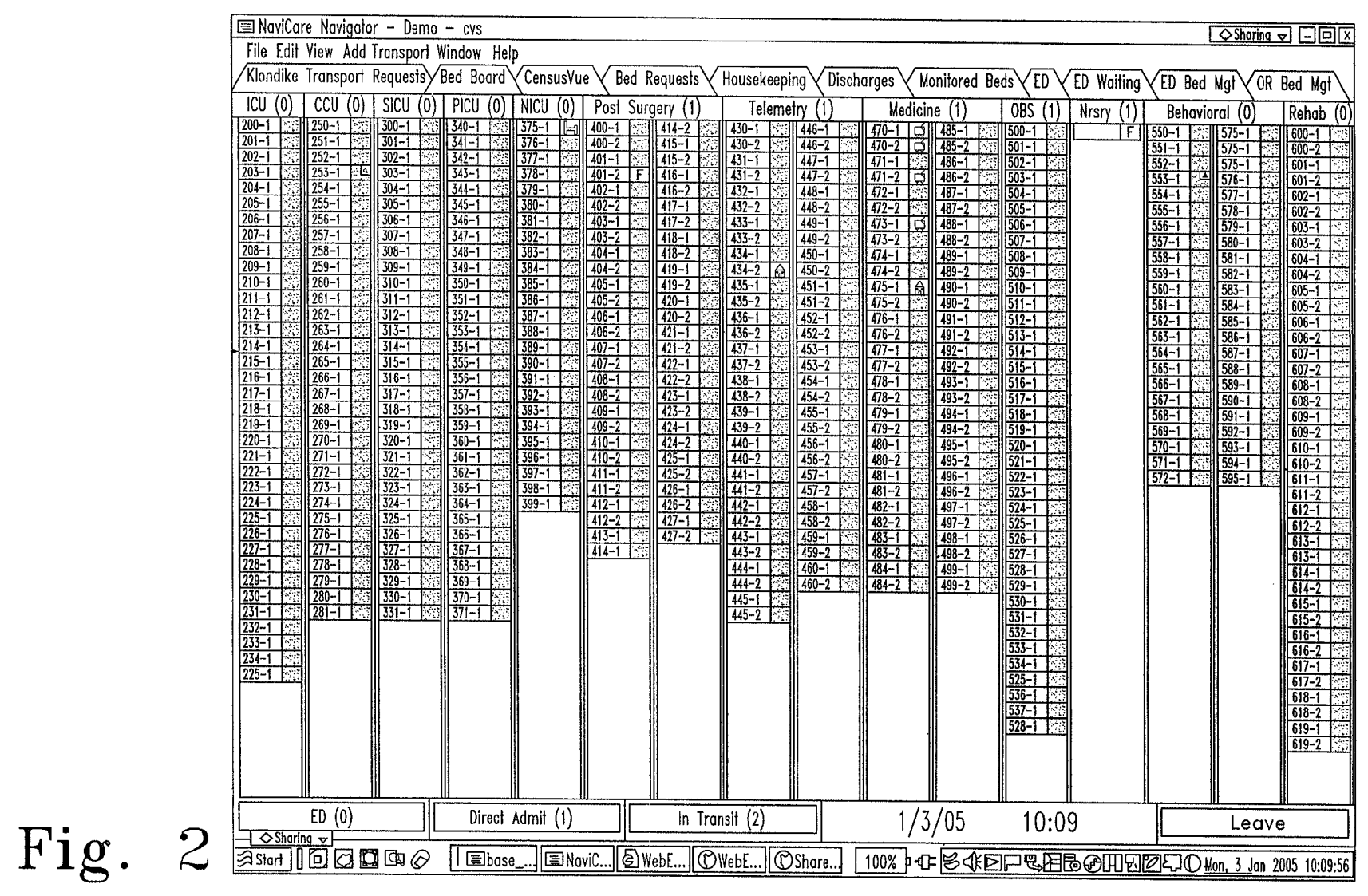

According to the present disclosure, the workflow software executed by server 14 includes a shortest-path algorithm as one of the decision making criteria for assigning tasks to persons on the medical staff. As shown illustratively in FIG. 2, a healthcare facility includes a number of zones, such as units, wings, or other areas of the facility. Some of the zones have multiple rooms within the zone. In the illustrative example, the healthcare facility includes the following zones: ICU, CCU, SICU, PICU, NICU, Post Surgery, Telemetry, Medicine, OBS, Nursery, Behavioral, and Rehab, as indicated by the text at the top of the columns of the table shown on the screen shot of FIG. 2. Rooms within the zones are indicated by numerical designators, such as 200-1, 201-1, and so on.

When a person on the medical staff completes a task and communicates that fact to system 12 either by entering the appropriate information on one of PC's 18 or by use of the associated device 46, 68 as described above, server 14 and/or PC's 18 execute the workflow software to associate a location in the healthcare facility with the person for purposes of deciding what the next task to assign to the person should be. If the person is wearing one of tags 42, then the person's location can be ascertained by server 14 sending the appropriate query to server 30 of the locating and tracking system, for example, or by retrieving the location data from data storage device 16 if device 16 is updated periodically with location data from server 30 as described above. In connection with the execution of the shortest-path algorithm of the workflow software, and assuming there are no overriding criteria which outweigh the results of the shortest-path algorithm, the workflow software operates to assign to the person another task that is associated with a location in the facility closest to the person's current location, which is typically at or near the place where the person completed the previous task.

Figure 3:
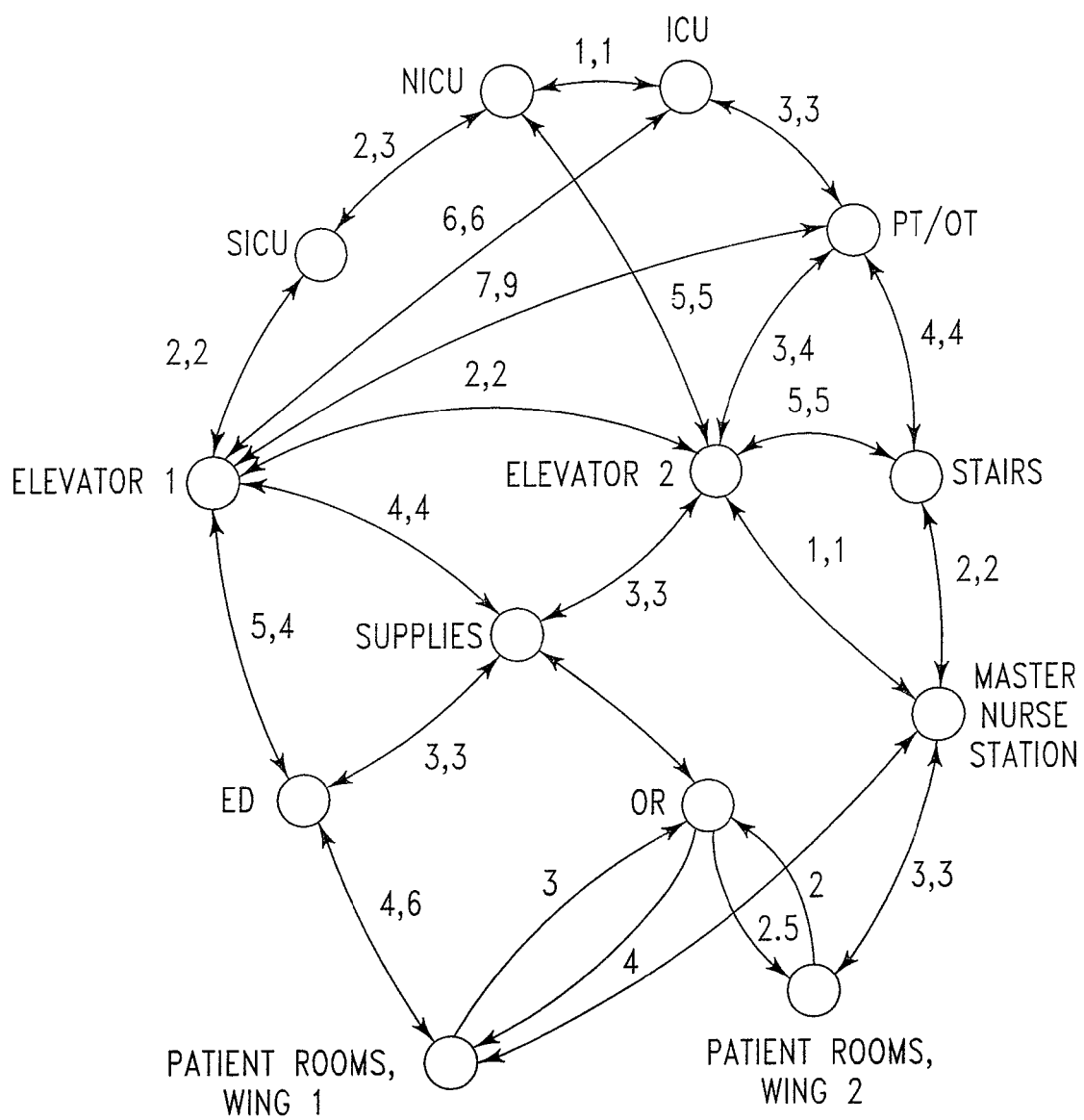
FIG. 3 is a diagrammatic view showing concepts associated with a shortest-path algorithm of the workflow software.

In one embodiment, the shortest-path algorithm is Dijkstra's algorithm. Dijkstra's alrorithm, which is an named after its discoverer E. W. Dijkstra, is an algorithm that is known in the field of computer science for finding the shortest path from one point on a graph to a destination point. To implement Dikjstra's algorithm in the workflow software of system 12, a mathematical model of the healthcare facility is created by assigning points (also referred to sometimes as vertices or nodes) to locations throughout the healthcare facility, as desired. Once the vertices are assigned, edge conditions (sometimes referred to as "edge weights") are assigned between various ones of the vertices. Edge conditions are numbers representative of either the estimated distance between two vertices at either end of the edge condition or the estimated time that is would take a person to travel from a point at one end of the edge condition to the point at the other end of the edge condition. Referring to FIG. 3, the circles represent assigned vertices and numbers adjacent to the arrowed lines between the circles represent edge conditions. Some of the vertices in FIG. 3 correspond to the zones shown in FIG. 2. If desired, vertices may be assigned to one or more of the individual rooms within any of the zones.

In the example of FIG. 3, the edge condition 3 is assigned from Patient Rooms, Wing 1 to the OR, and the edge condition 4 is assigned from the OR to Patient Rooms, Wing 1. This is an example of a bidirectional edge condition in which the edge condition in one direction is different than the edge condition in an opposite direction. The 3 and 4 between the OR and Patient Rooms, Wing 1 vertices indicate, for example, that it is estimated to take 3 minutes to transport a patient from Patient Rooms, Wing 1 to the OR but that it is estimated to take 4 minutes to transport a patient from the OR to Patient Rooms, Wing 1. The timing difference may be due to the fact that a different route may need to be taken in one direction than in another, or it may be due to the fact that the staff tends to transport patients more swiftly when going to surgery that coming from surgery.

Similar examples in which the edge conditions in one direction are not the same as the edge conditions going in the opposite direction are shown in FIG. 3 by the assignment of numbers 2 and 2.5 to the edge conditions between the OR and Patient Rooms, Wing 2 and by the assignment of numbers 4 and 6 to the edge conditions between the emergency department (ED) and Patient Rooms, Wing 1. In some instances, the edge conditions in both directions are the same, such as the example in FIG. 3 in which the number 3 is assigned as the edge condition in both directions between the Master Nurse Station and Patient Rooms, Wing 2. Double headed arrows are used in much of FIG. 3 to reduce the amount of clutter that would be present if separate single headed arrows were used. Transition points, such as elevators, escalators, stairs, ramps, corridors, and the like, may also have vertices assigned thereto. In the example of FIG. 3, vertices have been assigned to Elevator 1, Elevator 2, and the Stairs.

When a person of the medical staff indicates to system 12 that the person has completed an assigned task, the processor associated with server 14 executes the workflow software to determine the person's location and then designates the vertex which corresponds to the person's location as the "source" vertex. After the source vertex has been assigned to the person, the shortest-path algorithm is executed to determine the shortest distance path lengths (i.e., time-based or distance-based or both) between the source vertex and each of the other vertices in the facility. The path lengths may then be rank ordered from shortest to longest. System 12 then processes through the rank ordering from shortest to longest path length to determines the vertex that is closest to the source vertex and that has associated therewith a task which needs to be completed and which is assignable to the person of the medical staff.

Depending upon the role of the person on the medical staff, for example, nurse, housekeeping staff, maintenance staff, certified occupational therapy assistant, transporter, and so on, only certain tasks are assignable to the particular person. In some embodiments, prior to running Dijkstra's algorithm for purposes of determining a particular person's next task, system 12 eliminates any vertices which do not have an assignable task associated therewith. In alternative embodiments, other types of algorithms, such as any of a number of array sorting algorithms, which operate to calculate shortest path length between locations in a healthcare facility may be used in the workflow software of system 12 in lieu of Dikjstra's algorithm.

As alluded to above, there are some criteria that may outweigh the results of the shortest-path algorithm. For example, the workflow software may be configured so that if a particular task has not been completed after a predetermined maximum amount of time has elapsed, then that task may be prioritized ahead of other potentially assignable tasks regardless of the proximity of those other tasks to the persons on the medical staff capable of performing the task. Tasks which are critical to a patient's health may also take precedence over tasks that are in closer proximity to a person capable of performing the health critical task.

Figure 4:
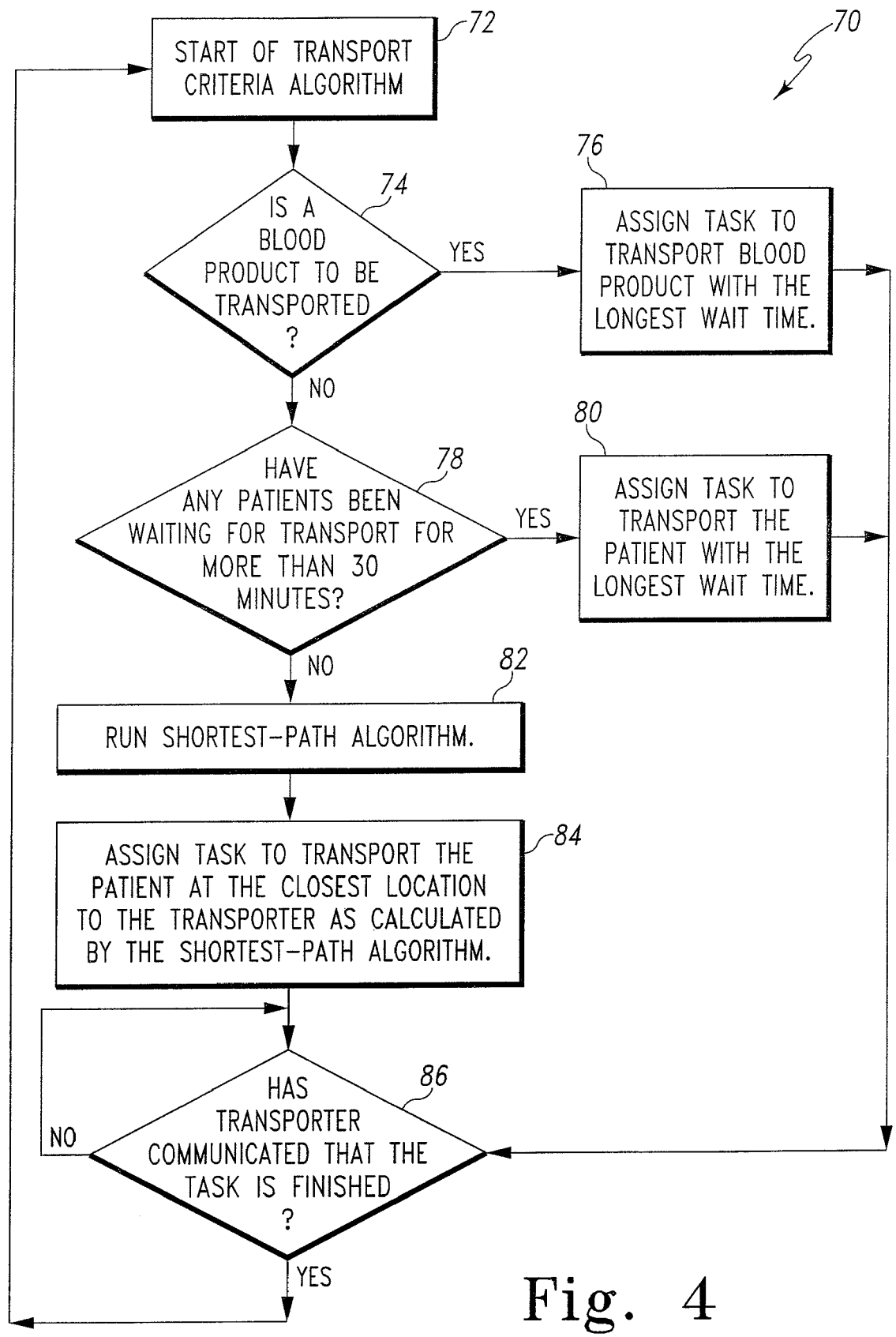
FIG. 4 is a flow diagram showing an example of an algorithm of the workflow software which operates to assign tasks to medical staff having the role of transporter.

An example of an algorithm 70 in which certain criteria outweigh the shortest-path criteria is illustrated in the flow chart of FIG. 4. Algorithm 70 is part of the workflow software executed by server 14 and/or PC's 18 and is but one example given for the purpose of illustrating the broader concept of a multi-criteria approach to assigning tasks to medical staff. In the discussion that follows, algorithm 70 will be described as being executed by server 14. However, algorithm 70, as well as portions thereof, may be executed by one or more of PC's 18 in lieu of, or in conjunction with, server 14.

Algorithm 70 is applicable to medical staff assigned the role of "transporter" for transporting patients, equipment, and supplies from place to place in the healthcare facility. After a transporter indicates to system 12 that a previous task has been completed, server 14 will, among other things, start a transport criteria algorithm as indicated at block 72. After starting algorithm 70 at block 72, server 14 determines whether a Blood Product needs to be transported as indicated at block 74. Blood Products may need to be transported, for example, from a hospital's blood bank to an operating room in which surgery is currently taking place. If at block 74, server 14 determines that one or more Blood Products need to be transported, then server 14 proceeds to block 76 and assigns to the transporter the task of transporting the Blood Product having the longest wait time. The wait time, for purposes of this example, is considered to be the amount of time that has elapsed after the initial transport request was made.

If at block 74, server 14 determines that no Blood Products need to be transported, then server 74 determines whether any patients have been waiting to be transported for more than 30 minutes as indicated at block 78. If at block 78, server 14 determines that one or more patients who need to be transported have been waiting for longer than 30 minutes, then server 14 proceeds to block 80 and assigns to the transporter the task of transporting the patient having the longest wait time. If at block 78, server 14 determines that none of the patients who need to be transported have been waiting for more than 30 minutes, then server 14 proceeds to run the shortest-path algorithm as indicated at block 82. After running the shortest-path algorithm, such as Dijkstra's algorithm described above, server 14 proceeds to block 84 and assigns to the transporter the task of transporting the patient at the closest location to the transporter as calculated by the shortest-path algorithm.

After server 14 assigns to the transporter one of the tasks associated with blocks 76, 80, 84, server 14 waits for the transporter to indicate to system 12 that the assigned task is finished as indicated at block 86. After the transporter indicates that the task is finished, then server 14 proceeds from block 86 back to the start of the transport criteria algorithm at block 72. In the FIG. 4 example, if a criteria which outweighs the shortest-path criteria exists as determined at blocks 74, 78, then the shortest-path algorithm is not executed by server 14. Bypassing the shortest-path algorithm in this manner saves computational time in server 14. It will be appreciated that hundreds, possibly thousands, of vertices may be assigned to locations in a healthcare facility in connection with creating the mathematical model of the healthcare facility that is used by the workflow software in executing the shortest-path algorithm.

A variety of events (not shown) may cause server 14 to interrupt algorithm 70 or to otherwise cause server 14 to exit from algorithm 70 and proceed to some other portion of the workflow software. For example, the transporter may go on break or may be finished with their shift. Thus, it will be appreciated that algorithm 70 is not an endless, continuous loop in the programming of the workflow software, but is shown this way in FIG. 4 for the sake of simplicity. Server 14 and PC's 18 may execute other routines and algorithms of the workflow software simultaneously with executing algorithm 70.

It will be appreciated that, in practice, the workflow software of system 12 will typically be programmed to consider a large variety of health critical criteria and to execute, possibly, a more sophisticated wait time criteria than is illustrated, prior to executing the shortest-path algorithm. For example, certain portions of the healthcare facility may be designated as being "near," "far," and "very far" from an area to which a person on the medical staff is assigned. Then different wait time thresholds may be associated with the near, far, and very far areas for a particular person on the medical staff. For example, a 30 minute wait time threshold may be associated with patients or equipment in near areas, a 1 hour wait time threshold may be associated with patients or equipment in the far areas, and 1.5 hour wait time threshold may be associated with patients or equipment in the very far areas. The given wait time thresholds are merely exemplary and other wait time thresholds may be used at the discretion of the programmer.

By having different wait time thresholds for different areas of the healthcare facility, there will be less of a tendency for persons on the medical staff to migrate to areas of the facility that are, perhaps, beyond the preferred area for the particular persons. In addition, the workflow software may be configured such that the shortest-path algorithm only calculates path lengths between the source vertex and vertices associated with near areas, or only with the near areas and far areas but not the very far areas, relative to the location of the source vertex. In addition, the workflow software may be configured such that, if a particular person has possession of a particular piece of equipment, then the only assignable tasks associated with that person are those tasks with which the piece of equipment is used. For example, some transporters may have a wheelchair with them. In such instances, the shortest-path algorithm may eliminate from consideration all tasks that do not require a wheelchair for the transport of a patient.

The information shown on the display screens in the prior art NaviCare® 5.2 system are typically room-centric (i.e., the screen shows a list of rooms and the patients, staff, and tasks associated with the room) or patient-centric (i.e., the screen shows a list of patients and the staff, tasks, and rooms associated with the patient). According to the present disclosure, the workflow software of system 12 has screens that are staff-centric.

Figure 5:
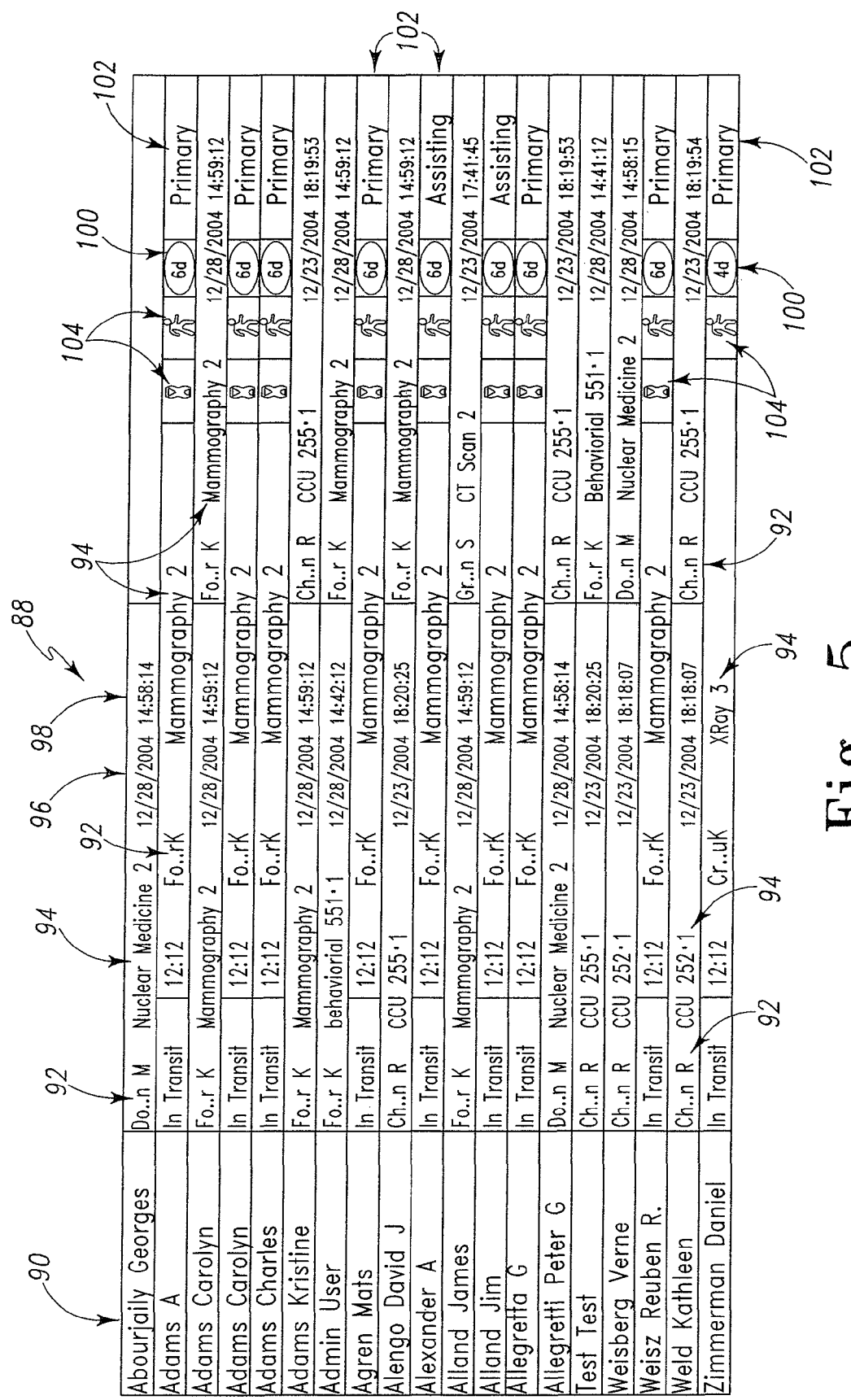
FIG. 5 is a screen shot of a staff screen which has been filtered by the workflow software based on medical staff role and sorted by the workflow software based on medical staff name.

One example of a staff-centric screen is shown in FIG. 5 as staff screen 88. The displayed data on screen 88 is filtered by medical staff role and sorted by medical staff identification. In the illustrative example, the filtering criteria for screen 88 is the medical staff role of "transporter" and the sorting criteria for screen 88 is the names of the persons on the medical staff who are designated as transporters. Thus, screen 88 shows a table having a first column 90 including cells in which the names of the transporters are listed in alphabetical order based on last name. Next to each transporter's name is a row of one or more cells that contain a variety of data including encrypted name data 92 of patients associated with the transporter, the rooms 94 in which the patients are located or are to be transported, date data 96, time data 98, wait time data 100, additional role data 102 (e.g., primary or assisting transporter), and various task icons 104. In the illustrative example, each of the hourglass icons indicate that a delay in transport has occurred and each of the person walking icons indicate either that a transport is needed or that a person is on the way.

The types of information that appear in the cells next to each medical staff identification is at the discretion of the system programmer or the system user. In addition, the medical staff identification field can be populated with some other type of data for medical staff identification, such as, for example, employee identification number, in lieu of being populated with employee name. Of course, cells in the staff-centric screens could be populated with both employee name and employee identification number, if desired. Furthermore, if the sorting function is based on employee name, then the sort can be in alphabetical order or reverse alphabetical order based on the first name or the last name of the medical staff, for example, at the option of the system programmer or the system user.

According to this disclosure, medical staff can be assigned to patients, procedures, locations, and/or zones. The type of information that appears on a staff-centric screen for a particular person of the medical staff, therefore, may be dependent upon whether the particular person of the medical staff has been assigned to one or more patients, procedures, locations and/or zones. Furthermore, the time frame for which information appears on the staff-centric screens may be at the discretion of the system programmer or system user. For example, the start time and/or date and ending time and/or date may be specified such that only tasks falling between the start time and end time appear on the staff-centric screens. Additional details of how a programmer may configure one or more staff-centric screens are shown and described in the Appendices forming part of U.S. Provisional Patent Application Ser. No. 60/642,775 to which the present application claims priority and which is incorporated by reference herein.

Although certain illustrative embodiments have been described in detail above, variations and modifications exist within the scope and spirit of this disclosure as described and as defined in the following claims.

The invention claimed is:

1. A computer-implemented method for managing workflow including assigning tasks to medical staff in a healthcare facility, the method comprising receiving information indicating that a person on the medical staff has completed an assigned task, ascertaining the person's location in the healthcare facility, and assigning a new task to the person based on a set of criteria including the person's location and including an amount of time that a task has remained uncompleted, wherein a task that is farther away from the person is assigned to the person as the new task if it has remained uncompleted for a threshold amount of time despite the fact that the person is closer to at least one other location having an associated task, and wherein the new task assigned to the person is a task that is closest in location to the person if the threshold amount of time has not elapsed for any tasks that are farther away from the person.

2. The method of claim 1, wherein receiving information indicating that the person on the medical staff has completed the assigned task comprises receiving information via an interactive voice response (IVR) system.

3. The method of claim 2, wherein receiving information via the IVR system comprises receiving voice information via a wireless communication device carried by the person.

4. The method of claim 2, wherein receiving information via the IVR system comprises receiving voice information via a telephone of the healthcare facility.

5. The method of claim 1, wherein ascertaining the person's location in the healthcare facility comprises ascertaining the person's location based on a wireless signal received from a portable device carried by the person.

6. The method of claim 5, wherein the portable device comprises a badge worn by the person.

7. The method of claim 1, wherein ascertaining the person's location in the healthcare facility comprises associating the person's location with a monitoring station at which the person enters the information indicating that the person has completed the assigned task.

8. The method of claim 1, wherein the set of criteria includes whether the person is in possession of a particular type of medical equipment.

9. The method of claim 1, wherein the set of criteria includes a role that has been assigned to the person.

10. The method of claim 1, wherein the set of criteria includes an amount of time that a patient or a piece of equipment has been waiting to be transported from one location to another.

11. The method of claim 1, wherein ascertaining the person's location in the healthcare facility comprises receiving data regarding the person's location from a locating and tracking system.

12. A computer-implemented method for managing workflow including assigning tasks to medical staff in a healthcare facility, the method comprising receiving information indicating that a person on the medical staff has completed an assigned task, ascertaining a first zone of the healthcare facility in which the person is located, and assigning a new task to the person based on a set of criteria including whether the person has a piece of equipment needed to accomplish a particular task and including an amount of time that a task in a second zone of the healthcare facility has remained uncompleted, wherein the task that is in the second zone is assigned to the person as the new task if it has remained uncompleted for a threshold amount of time despite the fact that the person is in the first zone, and wherein the new task assigned to the person is a task that is within the first zone if the threshold amount of time has not elapsed for any tasks that are in the second zone.

13. The method of claim 12, wherein the piece of equipment comprises a wheelchair.

14. The method of claim 12, wherein tasks that do not require use of the piece of equipment are excluded from being assigned to the person as the new task.

15. The method of claim 12, wherein receiving information indicating that the person on the medical staff has completed an assigned task comprises receiving information via an interactive voice response (IVR) system.

16. The method of claim 15, wherein receiving information via the IVR system comprises receiving voice communications via at least one of a wireless communication device carried by the person, a telephone of the healthcare facility, or a computer devices having voice communication capability.

17. The method of claim 12, wherein ascertaining a first zone of the healthcare facility in which the person is located is based on a wireless signal received from a portable device carried by the person.

18. The method of claim 12, wherein ascertaining a first zone of the healthcare facility in which the person is accomplished by associating the person's location with a monitoring station at which the person enters the information indicating that the person has completed the assigned task.

19. The method of claim 12, further comprising designating areas of the healthcare facility as being a near area, a far area, and a very far area from the first zone and assigning different wait time thresholds for the near, far, and very far areas in connection with assigning the new task to the caregiver.

20. The method of claim 19, wherein a first wait time threshold is assigned to the near area, a second wait time threshold longer than the first time threshold is assigned to the far area, and a third wait time threshold longer than the second time threshold is assigned to the very far area.

* * * * *